(12) United States Patent
Sevy (10) Patent No.: US 9,895,464 B2
(45) Date of Patent: Feb. 20, 2018

(54) AXIAL, TRIPLE-SEPARATION, DIFFUSION APPARATUS AND METHOD

(71) Applicant: Earl Vaughn Sevy, Cedar City, UT (US)

(72) Inventor: Earl Vaughn Sevy, Cedar City, UT (US)

( * ) Notice: Subject to any disclaimer, the term of this patent is extended or adjusted under 35 U.S.C. 154(b) by 163 days.

(21) Appl. No.: 14/850,789

(22) Filed: Sep. 10, 2015

(65) Prior Publication Data

US 2016/0000959 A1    Jan. 7, 2016

Related U.S. Application Data

(63) Continuation-in-part of application No. 13/854,545, filed on Apr. 1, 2013, now Pat. No. 9,415,130.

(51) Int. Cl.
*A61L 9/14* (2006.01)

(52) U.S. Cl.
CPC ..................... *A61L 9/14* (2013.01)

(58) Field of Classification Search
CPC ..................... A61L 9/00; A61L 9/14
See application file for complete search history.

(56) References Cited

U.S. PATENT DOCUMENTS

| | | | |
|---|---|---|---|
| 2,826,454 A | 3/1958 | Coanda | |
| 3,112,074 A | 11/1963 | Green | |
| 3,515,966 A | 6/1970 | De Valroger et al. | |
| 4,235,611 A | 11/1980 | Brownell | |
| 4,243,396 A | 1/1981 | Cronenberg | |
| 4,976,259 A | 12/1990 | Higson et al. | |
| 5,029,759 A | 7/1991 | Weber | |
| 5,054,477 A | 10/1991 | Terada et al. | |
| 5,201,641 A | 4/1993 | Richer | |
| 5,248,448 A | 9/1993 | Waldron et al. | |
| 5,309,900 A | 5/1994 | Knoch et al. | |
| 5,314,529 A | 5/1994 | Tilton et al. | |
| 5,549,247 A | 8/1996 | Rossman et al. | |
| 5,579,758 A | 12/1996 | Century | |
| 5,687,710 A | 11/1997 | Ambrosio et al. | |
| 5,875,774 A | 3/1999 | Clementi et al. | |

(Continued)

FOREIGN PATENT DOCUMENTS

JP           2001046920           9/2002

OTHER PUBLICATIONS http://www.air-aroma.com/diffusers.

(Continued)

*Primary Examiner* — Donald R Spamer
(74) *Attorney, Agent, or Firm* — Pate Baird, PLLC (57) ABSTRACT

A reservoir containing an essential oil feeds to an eductor injecting a jet forming a plume of air entraining oil droplets. A series of drift chambers act as velocity reducers to alternately slow the flow droplets with entry, and then reaccelerate them upon exit through an exit channel. A micro cyclone separator operates between at least two of the drift chambers, exposing the flow to circumferential direction and centripetal acceleration driving comparatively larger droplets out of the flow away from comparatively finer droplets sufficiently small to remain with the flow of air. Separation of comparatively larger droplets, effectively eliminates "spitting" of liquids that might or rapid drift onto surrounding surfaces.

20 Claims, 4 Drawing Sheets

(56) References Cited

U.S. PATENT DOCUMENTS

| | | |
|---|---|---|
| 5,922,247 A | 7/1999 | Shoham et al. |
| 6,029,913 A | 2/2000 | Stroia et al. |
| 6,236,042 B1 | 5/2001 | Kato et al. |
| 6,669,176 B2 | 12/2003 | Rock |
| D491,259 S | 6/2004 | Garrison et al. |
| 6,968,069 B1 | 11/2005 | Zhao |
| 7,712,683 B2 | 5/2010 | Robert et al. |
| 7,878,418 B2 | 2/2011 | Sevy |
| 7,930,068 B2 | 4/2011 | Robert et al. |
| 8,001,963 B2 | 8/2011 | Giroux |
| 9,415,130 B2 | 8/2016 | Sevy |
| 2008/0283049 A1 | 11/2008 | Mahoney et al. |
| 2010/0084484 A1* | 4/2010 | Sevy .................. A61M 11/06 239/4 |
| 2013/0327323 A1 | 12/2013 | Rubin |

OTHER PUBLICATIONS http://www.prolitec.com/appliances_commercial.htm.
http://scentair.com/why-scentair-solutions/.
http://www.brandaroma.com/products/.
http://www.e2aroma.com/appliances/smart-air-maxi/.
http://www.scentaustralia.com.au/index.php/products/scent-diffuser-zephyr.
http://www.voitair.com/scent-systems.
http://www.fragrancemachine.com/.

\* cited by examiner

AXIAL, TRIPLE-SEPARATION, DIFFUSION APPARATUS AND METHOD

RELATED APPLICATIONS

This application is a continuation in part of U.S. patent application Ser. No. 13/854,545, filed on Apr. 1, 2013, which is hereby incorporated by reference.

BACKGROUND

1. Field of the Invention

This invention relates to use of essential oils and, more particularly, to novel systems and methods for diffusers distributing atomized and vaporized essential oils from a reservoir.

2. Background Art

Mechanisms exist for altering a closed environment such as a room or home with humidity. Likewise, mechanisms exist for removing humidity. Electronic and chemical mechanisms for destroying microbial sources of scents exist. Meanwhile, sprays, evaporators, wicks, candles, and so forth also exist to distribute volatile scents, essential oils, liquids bearing scents, and so forth. These may be introduced into breathing air, an atmosphere of room, or any other enclosed space.

Heating often destroys or at least changes the constitution of essential oils. Thus, it has limitations. However, the evaporation rates or atomization rates of essential oils are often insufficient to provide a controllable, sustainable, and sufficient amount of an essential oil into the atmosphere. Thus, wicks having no air movement mechanism often prove inadequate.

Meanwhile, mechanisms that seek to copy vaporizers and moisture atomizers often damage surrounding equipment, furniture, and other environs of a space being treated by essential oils. Moreover, the continuing "spitting" by atomizers of comparatively larger droplets not only causes damage to finishes on surrounding surfaces, but wastes a substantial fraction of the essential oil.

Essential oils are concentrated sources of aromas or scents. Their extraction from source plants is sometimes complicated, and always comparatively expensive, based on the cost per unit volume of the essential oil. Therefore, colognes, other fragrancing systems, and the like often use high rates of diluents for essential oils. They also use synthetic oils and artificial scents that may not replicate the comforting, familiar, and natural essence of essential oils.

By whatever mode, systems to distribute essential oils often waste an expensive commodity while damaging surroundings about their atomizers or other distribution systems. Thus, it would be an advance in the art to provide an apparatus and method for distributing essential oils in as small particles as possible, preferably vaporized, while protecting surrounding areas. It would be an advance to do so while retrieving and recycling for re-atomization or diffusion any droplets that are larger than those that may be sustained by effectively Brownian motion once discharged into surrounding air.

BRIEF SUMMARY OF THE INVENTION

In view of the foregoing, in accordance with the invention as embodied and broadly described herein, a method and apparatus are disclosed in one embodiment of the present invention as including a reservoir fitted with an extraction system for drawing out of the reservoir and feeding into a diffuser nozzle. The nozzle may operate as an eductor. In fact, in certain embodiments an eductor may include an injection nozzle feeding into a plenum which plenum feeds through a diffuser nozzle toward an ultimate discharge point or port.

In certain embodiments, a system may include separation or drift chambers. For example, an initial separation chamber may actually be an evacuated space or vapor space near the top of a reservoir. This provides the advantage of the reservoir directly relying on contact accumulation, coalescence by contact between an atomized spray and the content of essential oil in the reservoir.

Typically, a sealed or flow-controlling cap may serve as a separator between this initial separation (drift) chamber, and other "downstream" separation (drift) chambers between the initial separation (drift) chamber and the ultimate discharge port. In various embodiments, changes of direction may serve as separation mechanisms. Thus, for example, the atomized flow composed of atomized essential oil and entraining air (air entraining those droplets and carrying them therewith) may pass as an atomized flow or simply flow through a circuitous route.

Changes in direction may be relied upon to coalesce out large droplets as they impact against striking surfaces. Striking surfaces may be naturally occurring walls of conduits, the reservoir, and so forth. However, striking surfaces may also be made up of baffles simply placed within a conduit or path in order to cause changes of direction, and to receive and coalesce overly large droplets. "Larger" means having too much mass, or rather too great a mass-to-surface-area ratio to drift indefinitely in air. This may also be expressed as a volume-to-surface-area ratio.

For example, a sphere has a volume. That volume is related to a third power of radius of the sphere. Thus, four thirds it multiplied by the radius to the third power equals the volume of a sphere having a radius of r. Meanwhile, the area of cross section (which controls air drag) is related to a second power or square of the radius. Surface area of the sphere is also related to the square of the radius. Thus, one can see that cross sectional area and surface area increase as the square of radius. Volume (proportional to mass and gravity force) increases as the cube. This means that as radius increases, mass (and gravity force) increases at a greater rate than area (proportional to drag) increases.

Conversely, this means that the decrease of radius decreases surface area as the square of radius, while decreasing volume as the cube of radius. Accordingly, there comes a point at which the cross sectional area controlling fluid drag of droplets in air is sufficiently large yet the mass and volume are sufficiently small, that a particle of such size may remain suspended indefinitely in air. That is, the drag forces resisting drift of the droplet downward with the force of gravity is sufficient to maintain indefinitely the drift of that droplet with the movement of air. Stated another way, the gravitational force is so miniscule as to be irrelevant to the time of drift. Gravity is unimportant. Drift can proceed effectively indefinitely.

Evaporation is an entirely different mechanism. In evaporation, individual molecules of a liquid become individual molecules of vapor. Vapors then abide by Dalton's law of partial pressures and take their place with other surrounding vapors including air, constituted primarily by oxygen and nitrogen. Thus, evaporated portions of an essential oil have performed well their function of distributing into the surrounding air.

Meanwhile, droplets sufficiently small to remain airborne substantially indefinitely, despite gravity, have also achieved their mission to distribute in air. Droplets too large, and therefore, too heavy, cannot be sustained in surrounding air against drift downward under the force of gravity. By drifting down these become the culprits in waste of essential oils and the damage to surrounding surfaces on which droplets land.

Thus, in an apparatus and method in accordance with the invention, it has been found that multiple separation (drift) chambers have proven effective to provide several key factors. For example, separation chambers provide time. The time of passage or containment of a droplet within a separation chamber provides opportunity for comparatively larger droplets to drift toward any coalescing surface. By coalescing surface is meant a surface upon which overly large droplets may strike, and coalesce with one another under the natural surface tension affinity that the essential oil has for itself.

Also, the separation chambers should provide inlets and outlets offset from one another. Inlets and outlets offset from one another offer changes of direction. Moreover, changes of direction imply barriers that will intercept overly large or "comparatively large" particles by serving as coalescing surfaces. Barriers may also redirect flows, thereby encouraging striking thereof by overly large particles.

Herein we will define overly large particles as particles that are larger, especially more than an order of magnitude larger in diameter than self-sustaining (permanently drifting) droplets. Thus, permanently drifting droplets are defined as droplets of an atomized liquid that are sufficiently small that they will not drift downward, especially the height of a room within a day of eight to twenty four hours. Thus, the finest particles, defined as permanently drifting particles are those whose gravitational acceleration under the force of gravity is insufficient to drift them down. Of interest also is any droplet that will not descend the height of a room within a day due to the resistance to drifting down by the fluid drag of the surrounding gases, such as room air. As a practical matter, droplets larger than these finest or permanently drifting particles are sufficiently small if they will drift with an airflow and leave with ventilation air. Often, air leaves a room in a matter of less than an hour.

For example, the American Society of Heating, Refrigerating, and Air Conditioning Engineering (ASHRAE) defines standards for room ventilation. Finest particles will necessarily be drifting with the flow of air and will leave a room before they have substantial opportunity to drift to the floor. Moreover, because room air is exchanged so frequently, typically more than once per hour, particles that are an order of magnitude larger than the finest particles also fit within the definition of comparatively smaller particles. In other words, these stay aloft for sufficient time to be swept out with the circulation of room air.

What is therefore needed to be controlled is the comparatively larger particles those that can drift to the ground in less than an hour or less than an air exchange time. The size may vary with temperature and with the specific gravity (density compared to the density of water) of a particular essential oil.

Thus, an apparatus and method in accordance with the invention may rely on a series of separation chambers. These may alternatively be referred to as drift chambers. These provide drift time for comparatively larger particles to drift toward and coalesce against striking surfaces.

In one embodiment, a parallel eductor, which is effectively a coaxial eductor, operates to inject or atomize a plume of educted gas or vapor (e.g., air) starting as a jet entraining therewith a certain amount of an essential oil to be atomized. This jet, proceeding out of the jet nozzle or injection nozzle (which initiates and creates the jet), passes through a receptacle or well. The well is drawing the essential oil out of the reservoir, through a tube into that receptacle.

The jet of air passing through the essential oil entrains a certain portion thereof, or entrains an essential oil at a rate and with sufficient energy to strip droplets from the surface of surrounding essential oil. It ejects those droplets with the jet through a diffuser nozzle.

Of course, according to the laws of physics and engineering, droplets are generated in a variety of sizes. Initially, the largest of the comparatively larger droplets will not be able to make the turn required to reverse direction. Reversal is required in order to pass back out through the cap and a channel in the cap that exits the vapor space above the reservoir.

In some respects the expression "co-axial" is not accurate. It refers to the fact that several elements literally share a central axis. Here, co-axial refers to the fact that a central axis passes through a reservoir and several separation chambers or drift chambers, and other components. However, they need not be symmetric, nor literally co-axial, but their flows' net directions are along a parallel, almost co-axial path. Meanwhile, the actual injection may be co-axial with the well and eductor nozzle, or may be parallel to the co-axial or central axis. In certain illustrated embodiments, the injection is nearly co-axial, but actually parallel.

The effect of this parallel or quasi co-axial injection is that the first coalescing surface that the comparatively larger droplets strike is not a surface of a solid at all. It is the upper surface of the supply of essential oil restored in the reservoir. This provides highly effective coalescence. It results in a comparatively large ongoing momentum transfer from comparatively larger droplets into the upper surface of the essential oil in the reservoir.

Effectively, this may also entrain air into the upper surface, causing a certain amount of bubbling or foaming at the upper surface of the essential oil in the reservoir.

Conservation of mass principles at work require that the air used for the jet in the eductor pass out of the vapor space in the reservoir. At least one channel is provided for that purpose. Meanwhile, there may exist a random action or trajectory of an overly large droplet toward any of the walls of the reservoir. Above the line or surface of the contained essential oil, this may result in those walls becoming coalescing surfaces. After coalescing overly large droplets, the walls continue draining them back into the essential oil contained in the reservoir.

The full change of direction, about 180 degrees, from the injection direction toward the surface of the essential oil to the pathway out through the exit channel, represents a first separation process. It is a direct-contact coalescence process. Droplets have direct contact with the content of the reservoir rather than coalescing with one another as each is smeared by impact against a coalescing surface.

Applicant hereby incorporates by reference: U.S. patent application Ser. No. 12/247,755, filed Oct. 8, 2008, issued Feb. 1, 2011, as U.S. Pat. No. 7,878,418, U.S. Design patent application Ser. No. 29/401,480, filed Sep. 12, 2011, issued May 29, 2012, as U.S. Design Pat. No. D660,951; U.S. Design patent application Ser. No. 29/401,517, filed Sep. 12, 2011, issued Sep. 4, 2012, as U.S. Design Pat. No. D666,706; U.S. patent application Ser. No. 13/854,545, filed Apr. 1, 2013; U.S. patent application Ser. No. 14/260,520, filed Apr. 24, 2014; U.S. Design patent application Ser. No. 29/451,750, filed Apr. 8, 2013, U.S. Design patent application Ser. No. 29/465,421, filed Aug. 28, 2013; and U.S. Design patent application Ser. No. 29/465,424, filed Aug. 28, 2013.

Each of these references, incorporated by reference herein in its entirety, discloses certain structures, components, controls, operating mechanisms, and designs for eduction and separation. In this application, Applicant need not, indeed cannot, reiterate all of the disclosure and illustrations contained therein. However, those references discuss various sizes and shapes of reservoirs, various types of caps and seals, various separation chambers, various striking surfaces or coalescing surfaces, and various paths and separation chambers. Those words are not necessarily used. Therefore, Applicant will hereby seek to define what is meant by these terms.

By a reservoir is indicated a supply, or a container for holding a supply, of an aromatic substance, such as an essential oil. By a diffuser is meant a system for atomizing and distributed comparatively smaller particles, including finest particles as defined hereinabove, and suitably fine particles that are within about an order of magnitude of the same diameter or radius as finest particles.

A jet is defined as in engineering fluid mechanics. A jet represents a flow of fluid having momentum, and passing through another fluid which may have the same or a different constitution. Thus, an air jet may pass through a surrounding oil. An air jet may pass through surrounding air. A significant feature of a jet is that it passes fluid having momentum through another fluid having a different specific momentum. Accordingly, momentum is exchanged between the environment and the jet, causing the jet to grow in size as a "plume." A plume will decrease in velocity as the momentum is distributed among more actual material (mass).

An eductor is a specific type of fluid handling mechanism. An eductor is a system in which a jet of a first constitution is injected into another fluid, typically of a different constitution. The momentum from the first jet is sufficient to cause the surrounding fluid entrained by the jet to continue as a plume of mixed constitution.

Herein, an eductor mechanism is created in which a jet, the source of that jet, and the surrounding environment into which the jet is injected are passed through an aperture. Any portion of the jet that exceeds the diameter or maximum dimension across the nozzle cannot pass therethrough, and thereby must recirculate back to be re-entrained in the jet, or to some other disposition.

A diffuser is in some respects an atomizer, but has the specific objective of producing finest fluid particles or droplets. Accordingly, a diffuser system includes not just an eductor but separation chambers, sometimes distinct separator structures. All are calculated to remove comparatively larger droplets, leaving only finest droplets and those within an about an order of magnitude thereof. Again, finest droplets or particles and comparatively larger particles have been defined hereinabove, in terms of their fluid dynamic behaviors. Those behaviors are defined by well established engineering equations. Therefore, all those equations are not repeated here. One may refer to textbooks and papers published on jets, atomization, fluid mechanics, two-phase flow, entrainment, plumes, and the like to obtain the details of the physics, the flow fields, the operational parameters, and governing equations for these phenomena.

Vapor space in a reservoir is defined as a portion of the volume of a reservoir container that contains other than predominantly the liquid for which the reservoir exists. That is, the vapor region actually contains air, a certain amount of the evaporated essential oil, according to Dalton's law of partial pressure in chemistry, and a certain quantity of drifting droplets in transit.

In certain embodiments of an apparatus and method in accordance with the invention, a reservoir may be fitted with an eductor injecting, through a diffuser nozzle, an entrainment jet containing both air, as the driving fluid, and atomized particles or droplets of the essential oil. An exit channel discharges some portion of the resulting flow from the vapor space out into a first drift chamber.

In one currently contemplated embodiment, all the drift chambers are effectively coaxial. The first drift chamber is the vapor space itself. Following passage through the exit channel from the vapor space, a second drift chamber provides time and a change of direction. It will permit the comparatively larger droplets to drift to a striking surface, coalesce thereagainst, and flow back toward the reservoir.

In certain embodiments, multiple channels connect drift chambers. Some may favor passage or exit of the entrainment air. Others may favor return of coalesced essential oil back toward the reservoir. Some may be shaped, bordered, leveed, or otherwise configured to favor, others to restrict, the flow of oil back toward the reservoir or to favor the flow of entrained droplets in air toward the discharge port. In certain embodiments, the drift chambers may include baffles, changes of direction, circuitous pathways, and the like. Various embodiments of these structures are illustrated in the documentation incorporated herein by reference.

By drift chamber is meant a region of space in which the effective cross sectional area of flow is increased above that immediately preceding entry into the drift chamber. Typically, this change in area may be double or more. However, the effective benefit of a drift chamber is a slowing of the air flow.

Mass flow rate is equal an area times the velocity passing through that cross sectional area, multiplied by a density of the material flowing. Volumetric flow rate is simply a velocity of the flow rate multiplied by the cross sectional area through which that flow passes.

Whether looking at mass flow rate or volumetric flow rate, area is a controlling parameter. Increasing area, while keeping the volumetric flow rate constant, requires that the velocity slow down. Accordingly, in order to slow the velocity, area is increased. The result of a change in velocity is to permit more time for comparatively larger droplets to drift out of their entraining airflow toward any adjacent wall, baffle, or the like.

Meanwhile, it is principally air that changes velocity. Comparatively larger particles injected into a drift chamber will typically drift right across it to the nearest and most direct striking surface to coalesce there. Thus, the drift chamber allows comparatively larger particles to drift quickly to a coalescing wall or surface. The slower air and those finest droplets entrained (those within the range of permanently drifting droplets), as well as some within an order of magnitude, slow down with the air and continue to flow through with the air toward the discharge port.

In certain preferred embodiments, a drift chamber exists immediately beyond the exit channel from the vapor space of the reservoir. Thereafter, the flow enters a separator. The separator may be thought of in some respects as a drift chamber. However, its purpose is quite different in certain presently contemplated embodiments.

For example, a micro cyclone is not actually a cyclone separator. Each operates on similar principles and acts as a separator. Here, in one presently contemplated embodiment, the actual micro cyclone separator does not slow the flow down, but maintains its speed at a comparatively high rate.

Air changes direction continuously about a circular pattern. The circular pattern is actually disposed on a spiral in which at one end of the spiral is an inlet and at the opposite is an outlet. Between them, the cross sectional area of the flow does not actually change significantly. However, the comparatively longer path provided around the micro cyclone provides centripetal forces forcing the comparatively larger droplets or particles toward the outside boundary of the micro cyclone. Acting as a centrifuge it throws those comparatively larger droplets out of the flow and against a coalescing surface in the micro cyclone.

Following the micro cyclone, operating as a separator, the flow of vapor or gas and entrained droplets passes through yet another drift chamber. It has been found that having three separate drift chambers is highly effective. Fluid velocities are intentionally slowed. The transiting flow slowing multiple times with multiple drift chambers provides the opportunity in each instance for the comparatively larger particles to strike a coalescing surface. Separation due to slowing and due to a direction change has been found very effective.

The addition of a separator, particularly the micro cyclone separator, has been found extremely effective to remove the comparatively large particles. Finally, the provision of contact coalescence by comparatively larger particles passing through the vapor space and into the surface of the standing liquid has also proven very effective.

Accordingly, it has been found that diffuser systems or diffusion system in accordance with the invention, operating with the structures and fluid mechanisms in accordance with the invention, provide three valuable benefits not found in prior art systems. First, comparatively larger droplets do not exit the discharge port and drift down upon surrounding surfaces. Second, this effectively diffuses and controls the amount of the essential oil diffused in order to provide a specific level of scent that is pleasant and effectively strong, without being overly strong.

Third, oil use required for a level of scent within a treated space has been shown to be much more efficient. That is, usage rates of less than half to a third of conventional systems result. Sometimes less than about one eighth to one tenth of conventional usage has resulted in systems in accordance with the invention.

In summary, the treated space has the properly controlled amount of the essential oil to provide the aroma and ambiance desired. Compared to prior art systems, whose rate of use is much greater, the essential oils are more efficiently used. Furniture and other surfaces are not damaged, sticky, or unsightly from comparatively larger particles drifting down onto them.

In various embodiments, an integrated system may be placed within a housing. It has been found that a reservoir may be fitted into one portion of the housing along with the multiple drift chambers and separators, all with the eductor nested within the same envelope (e.g., outermost dimensions of occupied space of the device). All are fitted neatly within typically about one half of the housing.

Meanwhile, pumps, batteries, power supplies, or the like have been fitted into the other side of the housing. This results in pleasant possibilities for design, along with compactness, uniformity, and convenience of integration.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 1 is a side, elevation, cross-sectional view of one embodiment of a coaxial, triple-separation, diffusion apparatus and method in accordance with the invention, illustrating a portion of a reservoir, contained essential oil, eductor, exit channel, micro cyclone separator, and drift chambers or separation chambers;

FIG. 2 is a perspective, partially exploded view of one embodiment of a reservoir, illustrating various sizes thereof, and specifically illustrating details of a micro cyclone separator intended to be placed within the flow path;

FIG. 3 is a schematic block diagram representing the side elevation view of one embodiment of a system in accordance with the invention, illustrating the directional and functional relationships between a reservoir, an eductor, the educted plume, a driving pump, and various drift chambers along with a distinct separator in accordance with the invention; and FIG. 4 is a perspective view of one embodiment of a system in accordance with the invention in a suitable housing, with various alternative shapes of that housing illustrated at the end of broken lines connected to one central embodiment.

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, an apparatus 10 or system 10 may include a housing 12, large or small. In fact, in the illustrated embodiment, the housing 12 may actually be configured as little more than a cap 12 secured to connect certain components to a pump 14 or a pump portion 14 of the system 10. In fact, in certain embodiments, the pump 14 may be remote from the housing 12. In other embodiments, the pump 14 is located within the housing 12.

Referring to FIG. 1, while continuing to refer generally to FIGS. 1 through 4, an atomizer 16 or eductor 16 draws from a reservoir 18, such as a bottle, large or small, typically of a conventional size in which such liquids 20 or essential oils 20 are commercially available.

In the illustrated embodiment, an exit fitting 22 or fitting 22 acts as a terminus 22 for introducing micro-atomized droplets of the essential oil 20 into a surrounding atmosphere or environment. Typically, atomization processes do not literally "atomize." Fluids are not subdivided down to an atomic level. Nevertheless, the conventional terminology of atomization refers to breaking apart a continuous supply, reservoir, or flow of a liquid 20 into airborne droplets.

However, atomization provides a distribution, typically a Gaussian distribution of droplets exiting from any atomization system. It has been found by the inventor that typical atomization systems are wholly inadequate for working with essential oils. First, essential oils tend to be solvents for service finishes on furniture. Essential oils may be reactive with plastics, other polymers, and the like. Moreover, essential oils may embed into fibers in carpets, rugs, and fabrics and evaporate, thus staining fabrics and other materials.

In the system 10 in accordance with the invention, it is desired to discharge from an exit port 23 exiting the exit fitting 22 only those droplets that are "comparatively smaller" as defined herein. As discussed hereinabove, comparatively larger droplets are considered those that will drift out of a surrounding air environment sufficiently fast. They have sufficiently high diameters to leave an oil residue behind out of the essential oil 20 discharged.

Comparatively smaller droplets are those smaller than the comparatively larger droplets. The idealized exit droplets are those that have the ability to remain in aerosol suspension for longer than the environmental ventilation requires to sweep them out with ventilating air. This is typically a period of time of about one hour. However, in certain embodiments, an apparatus 10 in accordance with the invention may typically discharge droplets (finest droplets) that are so small that they will remain indefinitely in a surrounding airflow. This is because the droplets have been subdivided or comminuted to a size sufficiently small. They have such a high fluid drag in moving through air, that the fluid drag forces of dropping with the force of gravity overcome the force of gravity, and thus maintain the micro-atomized (finest) droplets in the air basically indefinitely.

Thus, comparatively larger droplets are those that will drift out within the vicinity of an apparatus 10 leaving liquids on surrounding surfaces within a period of minutes to less than an hour. In contrast, the comparatively smaller droplets are those that will not drop out of air in a room. They stay airborne typically for at least an hour or the time dictated by the ventilation air exchange, for example, in a room.

The micro-atomized droplets are those droplets that will not drift out of air, but remain ineffectively indefinitely. Comparatively small droplets are smaller than the comparatively larger droplets. It is one objective and benefit of an apparatus 10 in accordance with the invention to produce a high fraction of micro-atomized droplets, and to substantially eliminate any comparatively larger droplets from exiting out the exit port 23 of the apparatus 10. This defines at least three size ranges, substantially distinct.

A liquid surface 24 lying at the top of a reservoir 18 of an essential oil 20 divides the liquid essential oil 20 from overlying air. A tube 26 or siphon 26 extends down below the surface 24 of the liquid 20 to draw therefrom.

By eduction, the tube 26 siphons or draws the liquid 20 up the tube 26 or siphon 26, and into a well 28. The well 28 actually may discharge into a vapor space 30 operating as a first drift chamber 30. That is, the vapor space 30 is filled with air, some vapor, according to Dalton's law of partial pressures of vapors. The space 30 contains vapors resulting from the evaporation to vapor of a certain portion of the liquid 20. It also contains droplets that have been educted into that vapor space 30 or drift chamber 30.

Eduction is accomplished by the eductor 16, beginning with a nozzle 32, which may be thought of as an air nozzle 32 creating a jet of air. The jet 33 may be thought of as a thin flow of air at a comparatively high velocity being injected by the nozzle 32 or air nozzle 32 toward the vapor space 30. The vapor space 30 is typically substantially quiescent with respect to the comparatively higher velocity of the jet 33 emanating from the air nozzle 32.

The nozzle 32 is driven or fed by a line 34 bringing air from the pump 14. The line 34 may be represented by a path 34 through multiple components, such as solid tubes, flexible tubes, hoses, pipes, or the like. All of these may contribute to or become a portion of the line 34 connecting a pump 14 to an air nozzle 32.

An eductor nozzle 36 is not required in every eductor 16, but provides a significant benefit. For example, systems much larger than a diffuser apparatus 10 in accordance with the invention may use the principle of eduction. In fact, eduction may be used to move large bodies of fluid in industrial plants. Eduction may be used to effectively pump comparatively larger conduits of fluid by injection of small, comparatively higher velocity jets of a cleaner fluid more adapted to be pumped.

Thus, here, the eductor nozzle 36 provides a certain amount of containment of the jet 33, and of the surrounding liquid 20 drawn into the well 28. Eduction happens by the jet 33 from the nozzle 32 passing outward through the liquid 20 in the well 28. The jet 33 thereby entrains from the surrounding surface of that liquid 20, droplets stripped off by the turbulent airflow at the boundary of the liquid 20 passed by the jet 33.

One property of jets 33, from a fluid engineering point of view, is that a jet 33 is a flow of one fluid of higher momentum through a surrounding environment of a fluid of different momentum, which may be the same or different type of fluid. Thus, one may have a jet of hot water rising through a surrounding environment of colder water. Jets may be air in water or water in air. One may have a jet of high speed water impinging on a reservoir of quiescent or slower flowing water.

Here, the jet 33 constituted by air coming from the nozzle 32 passes out through the eductor nozzle 36, into the vapor space 30. It draws with it entrained quantities of the liquid 20, thereby blasting into many many droplets what was originally a continuous, contiguous liquid. Thus, the eductor nozzle 36 introduces the jet 33 containing both air and entrained droplets of oil 20 into the vapor space 30. The vapor space 30 operates as the first drift chamber 30 in a separation process.

The flow 37 of air and entrained droplets passes out from the vapor space 30 or drift chamber 30. Any amount of the liquid droplets 39 that strike a wall, drift downward out of entrainment with the air, or the like will either shatter, coalesce, or both. Coalesced oil will pass back through a drain 38 into the reservoir 18, and the liquid 20 contained therein. However, what remains in the flow 37 will exit the vapor chamber 30 toward another drift chamber 40 by way of a connecting channel 42.

A characteristic of each drift chamber 30, 40, and any interconnecting channels 42 is that each channel 42 constricts the flow by changing downward (reducing) the available cross sectional area of flow. Thus, each channel 42 effectively accelerates, or requires the flow 37 to accelerate to a higher speed in order to maintain a substantially constant flow of air through the entire pathway of the apparatus 10.

In the illustrated embodiment, the channel 42 has a much smaller cross sectional area than does the drift chamber 40, and a smaller cross sectional area than does the drift chamber 40. With each acceleration of flow through a channel 42, two benefits are obtained. First, pressure (static pressure, as that term is used in fluid engineering) reduces. Meanwhile, velocity increases. Then, each channel 42 typically casts its flow 37 into a subsequent drift chamber 40 where the flow 37 must slow and change direction.

The comparatively larger droplets tend to continue in the direction of their initial momentum through the channel. They often crash into or smash into an obstructing barrier, such as an adjacent wall, baffle, or the like. This causes the droplets 39 that strike solid surfaces to shatter, coalesce, or both at those surfaces. Surfaces collect oil and flow it back through the drain 38 to arrive back in the liquid 20 collected in the reservoir 18.

This provides the benefit of not only reducing the discharge of comparatively large droplets, substantially to zero in the experience of the system 10, but permitting the discharge from the exit port 23 of only comparatively smaller droplets. Restricting the discharge flow limits soil output to micro-atomized droplets that will drift sufficiently long, or even indefinitely, in surrounding air.

A separator 44 as used herein means a specific type of separator separate from a drift chamber 30, 40, 50. A drift chamber relies on at least one change of direction, surrounding walls to smash, subdivide, or collect comparatively larger droplets 39, and so forth. In that context, every drift chamber 30, 40, 50 is a separator 44 of sorts.

However, the separator 44 is specifically a low-aerodynamic-loss separator. Baffles lose energy and driving pressure. Abrupt obstruction all do. One such unique separator is designated as a micro cyclone separator 44. A micro cyclone 44, a coined term, is not actually a cyclone. Cyclone separators are used in certain industrial processes. Cyclone separators literally set up a vortex in a two-phase system. The two phases may be solid and liquid, solid and vapor (e.g., air, gas), vapor and liquid, and so forth.

Here, a micro cyclone 44 uses continual or sustained centripetal force as a separation mechanism. However, it does not permit an actual vortex, as that mechanism has shown to be ineffective in essential oil atomizer systems 10 such as a system 10 in accordance with the invention. It has been found that sufficiently high speeds with turbulent flow (terms of art in the fluid engineering technology, which may be understood by repair to any textbook on the subject) have a tendency to re-entrain comparatively larger droplets. This can be problematic.

It is desired in a system 10 and method in accordance with the invention to remove the comparatively larger droplets permanently, and not simply recycle them, re-entrain them, reaccelerate them, and re-smash them into obstructions. Rather, it is considered more effective to simply separate them out, coalesce them, and return them back to the liquid 20 in the reservoir 18. Thus, cyclone separators of conventional types do not permit the proper separation processes. In fact, one reason for the drain 38, is to provide an alternative path for liquid 20 draining back into the reservoir 18. It has been found more effective to remove larger droplets from downstream processes rather than accelerating and comminuting them, or risking re-entrainment by countercurrent flow between the returning liquid 18, and out going flow 37 of droplets 39. To permit significant counter flow throughout would invite turbulent stripping of droplets off the surface of liquid, thus reintroducing comparatively large droplets.

To be sure, the micro cyclone 44 does permit counter flow. However, due to the almost full circle, the micro cyclone 44 tends to throw droplets 39 radially outward against an outer wall. It may actually include a circumference path longer than a full circle. Liquid coalesces and drains back out of the spiral shape of the micro cyclone 44, eventually working its way back out through the drain 38 and into the reservoir 18.

The separator 44 is discussed in considerable detail in the patent applications incorporated herein by reference and identified hereinabove. It is sufficient to point out that the micro cyclone separator 44 illustrated provides a cleverly constructed device 44 having a top half 45a and bottom half 45b defining an entrance 46 and exit 48 of substantially the same cross sectional area. The conduit 52 therebetween traverses a spiral beginning at the entrance 46 receiving the flow 37 from the drift chamber 40, and transferring that flow about a centrifugally separating path about the circumference of a circle, discharging the flow 37 at the exit 48 into the drift chamber 50.

Here, the cross sectional area available for traverse or passage of the flow 37 through the drift chamber 40 is extremely large compared to the comparatively smaller cross section of the entrance 46 and exit 48 of the micro cyclone separator 44. Thus, once again, the separator 44 or micro cyclone 44, in this instance, operates as a conduit 52 or channel 52 requiring acceleration of the velocity of the flow 37. It discharges into a drift chamber 50 where that flow 37 will again be slowed to permit time for drifting. The flow 37 will change direction, providing another opportunity for any oversized droplets, or any other droplets 39, to strike walls.

It is important to understand that micro-atomized droplets 39 do not typically strike any surrounding solid surfaces. Of course, boundary layer theory is well documented in any text on the subject, and even in most texts directed to basic fluid mechanics. Such will explain how a thin boundary layer near any solid surface does tend to extend from a stationary fluid at the solid surface out to a free stream velocity in the principal flow passing thereby.

Nevertheless, the nature of micro-atomized droplets 39 makes them so small that they accelerate as the entraining air accelerates, and decelerate with the air when it slows due to the overwhelming dominance of fluid drag. This is directly in opposition to the behavior of the comparatively larger droplets 39. The comparatively larger droplets 39 instead have such momentum, that their drag forces (body drag or fluid dynamic drag as understood in the art of engineering fluid mechanics) are oppositely disposed. Drag forces on the comparatively larger droplets are not as comparatively large, in comparison with the gravitational forces and momentum forces. The comparatively larger droplets, once accelerated, do not readily change direction. They are typically smashed into walls in response to any abrupt change of direction. They tend to strike, comminute to smaller sized droplets, coalesce, or some combination thereof.

It has been found that a micro cyclone 44 in accordance with the invention is a very effective separator 44. It provides a comparatively long path (pi or arc of angle times the diameter of the circle that defines the conduit 52) or approximately that distance, all the while subjecting the flow 37 to a tight turn radius. By continuing for a sufficiently long time and path length, it permits comparatively larger droplets to drift under centripetal force outward to be coalesced, collected, and drained back into the reservoir 18.

The drift chamber 50 may be larger, smaller, or comparatively equal in size, path length, change of direction, change of cross sectional area, or the like with respect to the other drift chambers 30, 40. However, there is not a requirement that any drift chamber 30, 40, 50 be an exact size. The basic components are cross sectional flow area, a distance of travel permitting time for settling out a comparatively larger droplets, a change of direction (often both in and out), and an obstruction such as a wall, baffle, or the like. These capture comparatively larger droplets 39 that cannot make the changes of direction required by the flow 37 passing therethrough.

Meanwhile, the channel 54 requires a change in direction and velocity in order for the flow 37 to eventually find its way therethrough. Just as with the lower drift chamber 40, a channel 54 provides a path for the entraining air and droplets 39 of the flow 37. The drift chamber 60 also presents additional changes of direction, changes of cross section, and so forth. Likewise, the drift chamber 60 typically provides a drain 56 for return of fluids back "upstream" with respect to the direction of the flow 37 from the eductor 16 toward the exit port 23.

In certain embodiments, channels 42, 52, 54 may be provided with fences 58 or borders 58. Several different borders 58 are illustrated as examples 58*a*, 58*b*, 58*c*. A reference number represents a generic item, and the trailing reference letter identifies a specific instance when that is needed. A border 58 assists in maintaining separation.

For example, a border 58 or fence 58 may be placed to direct accumulated, coalesced liquid 20 away from channels 42, 52, 54. Oil is urged to return back through the drains 56, 38 to consolidate with the liquid 20 in the reservoir 18.

However, in order to further minimize stripping of additional comparatively large droplets from the surface of such returning liquids 20, drains 38, 56 may be separated horizontally from the channels 42, 52, 54. These drains may be sized smaller to encourage the flow 37 to pass through the channels 42, 52, 54, to the exclusion of the drains 38, 56.

Also, the fences 58 operate to reduce the tendency of returning liquid to drain down around the boundaries or edges of the channels 42, 54. This reduces the tendency for comparatively higher speed flows through the channels 42, 54 to be exposed to the liquids, and to engage in turbulence and entrainment of droplets stripped from the surface of the returning liquid 20.

Referring to FIG. 2, while continuing to refer generally to FIGS. 1 through 4, the principles of operation have been described for this embodiment of a system in accordance with the invention. Various drift chambers 30, 40, 60 may be built into the housing 12, the exit fitting 22, and so forth. Such embodiments as those illustrated in FIG. 1 are not shown in internal views in this illustrated embodiment. However, details of the micro cyclone 44 are illustrated, including, clockwise from the top, a top plan view, a front elevation view, a bottom plan view, and a rear elevation view. Meanwhile, an exploded view of the two halves 45*a*, 45*b* of the micro cyclone 44 is illustrated in the center of the other views.

Of course, various sizes of reservoirs 18*a*, 18*b*, 18*c*, 18*d* may be configured to fit within or outside of the housing 12. In certain embodiments, the reservoir 18 may be provided with some type of an adapter 64 that operates much as a cap 65 that would otherwise seal the reservoir 18. Here, an adapter 64 may be provided with threads 66 or another fitting 66 connecting to the housing 12 or other constituents required to connect to the upper drift chambers 40, 50, 60.

Referring to FIG. 3, while continuing to refer generally to FIGS. 1 through 4, a schematic diagram illustrates a system 10 in accordance with the invention in one embodiment. It has been found that a plume 70 is generated by the eductor 16. That is, for example, the jet 32 entraining droplets 39 of the liquid 20 in the stream of air from the pump 14 and line 34 continues to exchange momentum with the surrounding environment in the vapor space 30 or first drift chamber 30.

Plumes 70 are defined in the engineering art of fluid mechanics. One may repair to papers, textbooks, and treatises on the subject. A plume is effectively an expanding jet. A jet typically is modeled or represented as momentum injected into a surrounding environment. The jet begins to exchange momentum with the surrounding fluid, thereby creating a plume. The momentum originally embodied in the jet is exchanged with surrounding material, with some losses. Flowing that increasing amount of material forward in an ever-widening plume 70 reduces maximum velocity. That is, continuing to exchange momentum and pick up mass flow, results in slowing the maximum, central flow velocity. Total momentum cannot increase with widening the extent of the plume 70.

This plume 70 operates with the surface 24 of the liquid 20 as a capture device. Rather than smashing against a wall and coalescing with other droplets so disposed, the plume 70 discharges directly into the surface 24 of the liquid 20. The flow 37 is opposite and flow parallel to the exit flow 37. This abrupt and complete reversal of flow direction, immediately coalesces a certain fraction of the comparatively larger droplets 39 with the bulk of the liquid 20 in the reservoir 18.

Thereafter, only oil 20 in the flow 37 that has navigated the abrupt change of direction is still remained entrained in the air. It exits in the flow 37 through the channel 42 arriving at the drift chamber 40.

The flow 72 of air through the eductor 16 results in a flow 74 that has a somewhat variable constitution. Therefore, even though we discuss the flow 37 generically through the system 10, the constitution of the flow 72 is air. The constitution of the plume 70 is air entraining droplets 39 along a typical (e.g., Gaussian) distribution of droplets 39. This Gaussian distribution is truncated or filtered, so to speak, by entrapment of the comparatively larger droplets 39 in the liquid 20. Thus, the flow 74 has a different and changing constitution, as does the flow 37. Although constituting about the same amount of air, it does not constitute the same number nor the same size distribution of droplets 39.

Following the drift chamber 40, the flow 37, 76 has again been stripped of its comparatively larger constituents. Meanwhile, the separator 44 conducts its centripital operation, as described hereinabove. Thus, the flow 37, 78 reaching the final drift chamber 60 is further separated to include only the comparatively smaller droplets 39 in the flow 37.

One will note that the schematic illustration includes only three drift chambers. In contrast, the previous description included four. It has been found that a system 10 in accordance with the invention operates substantially better with three drift chambers than with two. With three drift chambers 30, 40, 50, 60 rather than two. Also, it has been found that a micro cyclone separator 44 between two of the drift chambers, such as drift chamber 40 and drift chamber 60 illustrated here tends to greatly improve the overall efficacy. Thus fluid pressure losses are reduced with three drift chambers removing the comparatively larger droplets. Three drift chambers 30, 40, 50, 60 where one uses contact removal, with a microcyclone separator provides excellent separation with acceptable pressure drop along the flow path. This results in restricting the flow 37 to contain only the comparatively small and the micro-atomized droplets 39.

Ultimately, the flow 80 discharged from the outlet port 23 preferably contains only micro-atomized droplets 39. As a practical matter, it has been observed that a system 10 in accordance with the invention, having the collinear or parallel but oppositely directed flows 33 and 37 within the vapor space 30 of the reservoir 18 is very effective as a first separation process. Meanwhile, having at least two other drift chambers 40, 50, 60, with a micro cyclone separator 44 between two of them has proven extremely effective. This reduces the use of essential oils 20 with no effective loss in aroma intensity in the space serviced by a diffuser 10 or system 10.

Thus, the effectiveness, the actual evaporation and sustained drifting of comparatively small and micro-atomized (finest) droplets 39 is achieved. This occurs without the loss of liquid represented by the temporarily drifting, comparatively larger particles that do not remain sustained in the air over comparatively long (e.g., air exchange times, often about an hour or more) in the air environment being treated by the diffuser 10.

Figure 1:
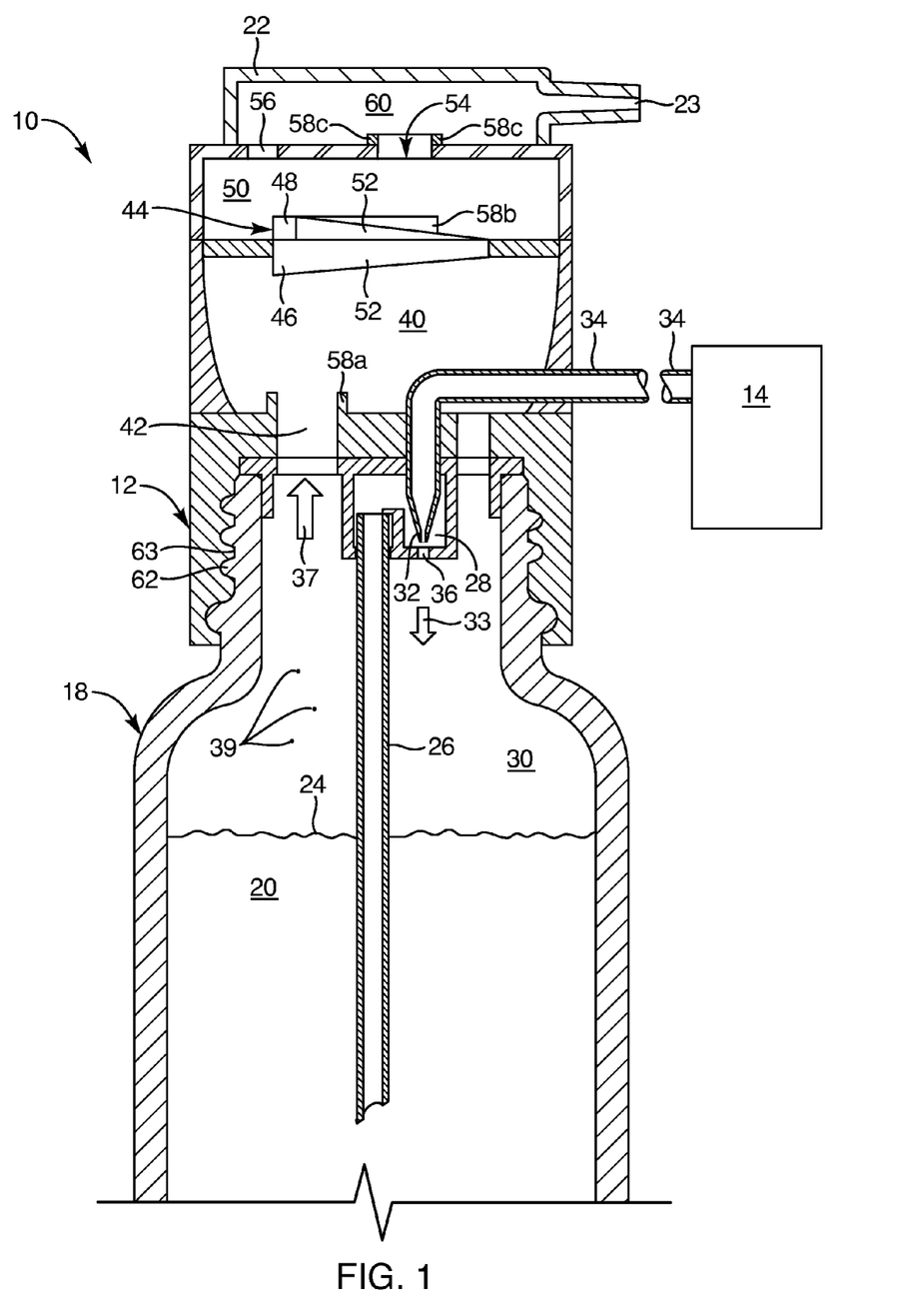
Figure 2:
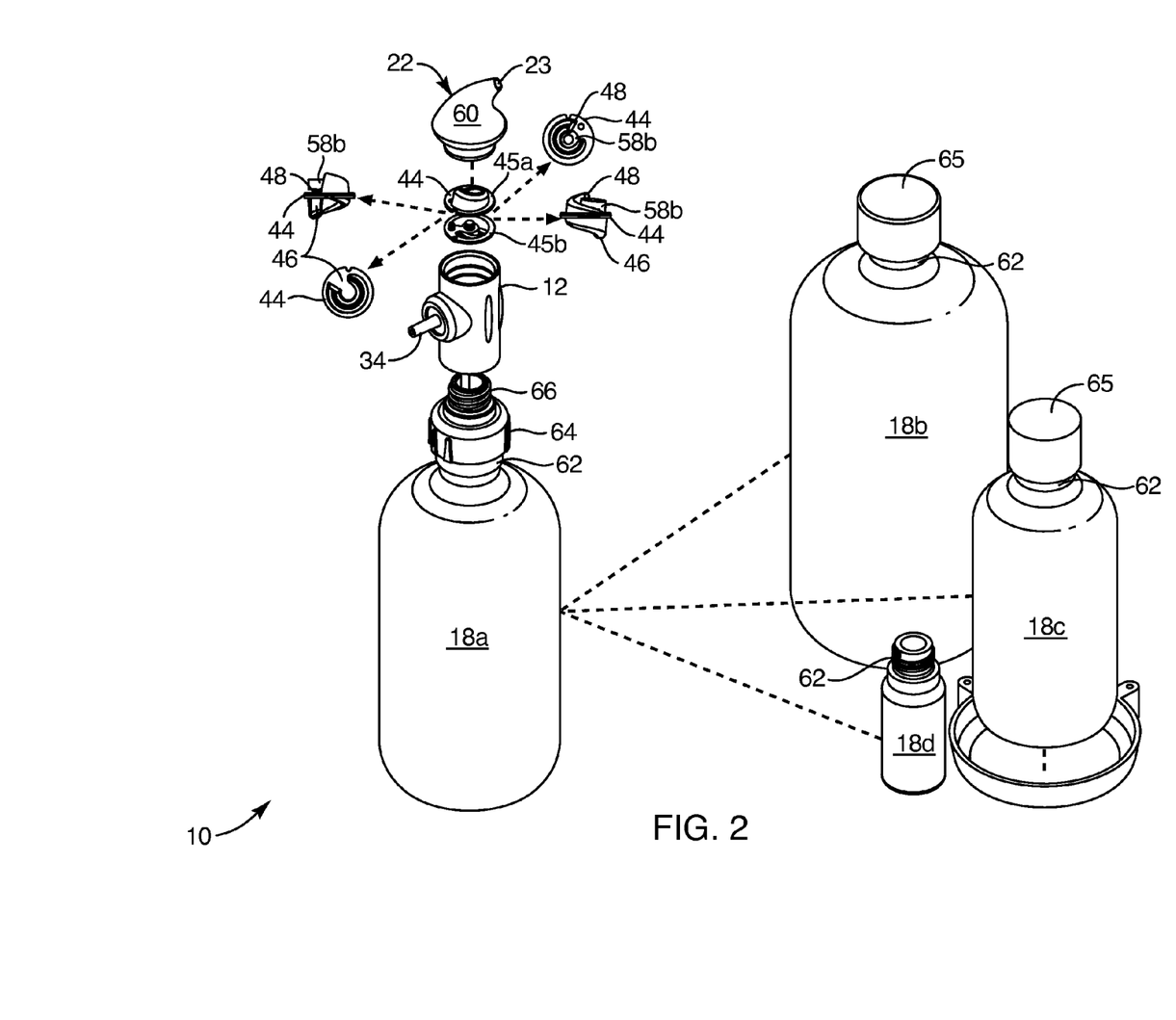
Figure 3:
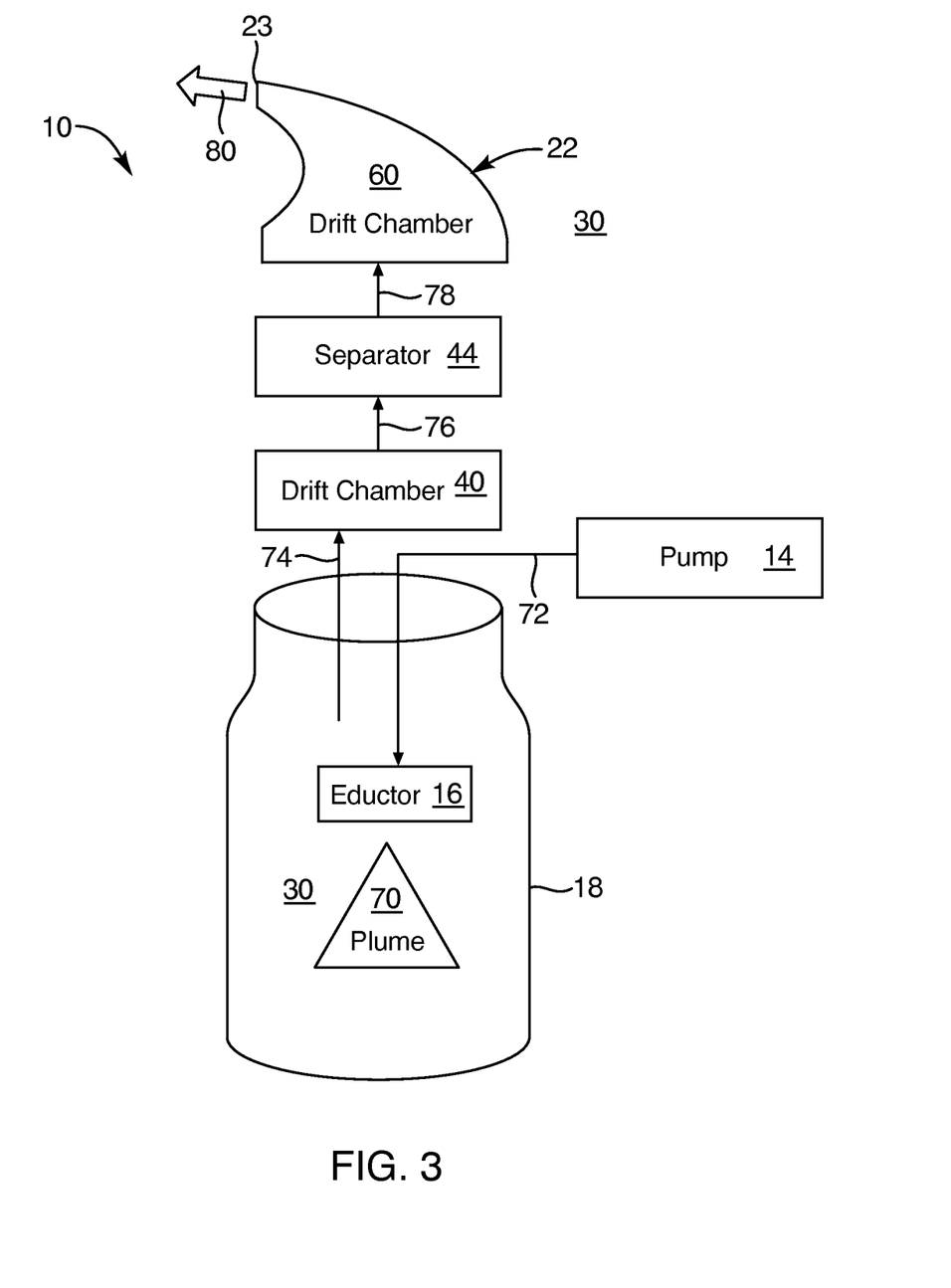
Figure 4:
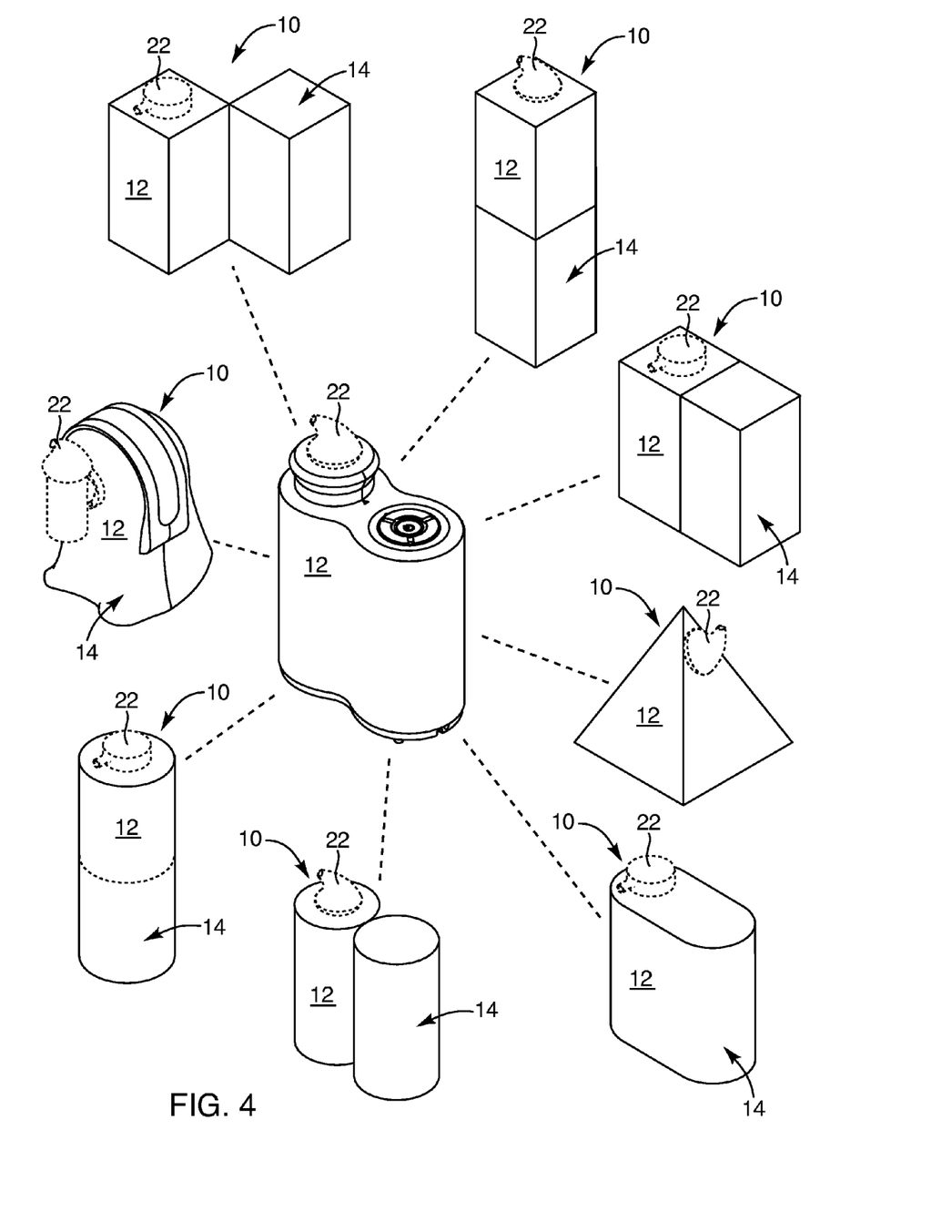

Referring to FIG. 4, while continuing to refer generally to FIGS. 1 through 4, various embodiments of housings 12 are illustrated, having space for a pump 14 integrated into the housing 12 with the drift chamber 30, 40, 50, 60 and the micro cyclone separator 44. Designs include various shapes, and various connection schemes operating in tandem, side by side, in various geometries, and even stacked axially. Various types of exit fittings 22 may be used, including those illustrated, and others.

Fluid communication between a pump 14 through a line 34 is necessary to provide a turbulent stream or jet 36 of air entraining droplets drawn from the liquid 20 and the reservoir 18, as described hereinabove. Nevertheless, integrated packaging provides a simple system in which such supporting structures as a pump 14, lines 34, and even the internal details of the drift chambers 30, 40, 50, 60, and so forth are neatly hidden from view, while operating effectively.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of diffusing an essential oil, the method comprising:
    providing a reservoir containing an essential oil, an eductor injecting a jet, forming a plume of entrained air and essential oil drawn from the reservoir, back into a vapor space in the reservoir;
    providing a source of air at a pressure above ambient pressure operably connected to drive the eductor;
    providing a first drift chamber operably connected to receive at least a portion of an output of the eductor and positioned in close proximity to the reservoir;
    providing a separator operable to separate out comparatively larger droplets from comparatively finer droplets of the essential oil;
    providing a terminal drift chamber operably connected to the separator and configured to reduce the flow velocity of air and entrained droplets of the essential oil prior to discharge from a discharge port of the terminal drift chamber, opposite the separator;
    providing a supply of pressurized air to the eductor from the source;
    educting the plume into the vapor space of the reservoir;
    separating out by the surface of the essential oil in the reservoir a portion of the comparatively larger droplets of the essential oil entrained by the pressurized supply of air;
    comparatively smaller with respect to the comparatively larger droplets absorbed into the essential oil in the reservoir;
    passing the flow through the first drift chamber;
    passing the flow through the separator; and
    exiting by the flow from the terminal drift chamber by a discharge port.

2. The method of claim 1, further comprising:
    passing the flow through the separator in a circular path and
    flowing the coalesced, comparatively larger droplets from the terminal drift chamber, the separator, and the first drift chamber to the vapor space.

3. The method of claim 2, wherein the circular path begins and ends at different axial levels along an axis through the circular path, the circular path thereby constituting a spiral path.

4. The method of claim 3, further comprising:
    applying a centripetal force to the comparatively larger particles passing through the separator effective to drive those comparatively larger particles toward an outer wall of the separator, and coalesce those comparatively larger particles thereat.

5. The method of claim 4, wherein providing a separator further comprises:
    providing a micro cyclone constituting a walled path of substantially constant cross section, and of greater than three quarters of a circle in the circumference.

6. The method of claim 1, further comprising:
    operating the first drift chamber directly above the reservoir.

7. The method of claim 6, further comprising:
    positioning the terminal drift chamber above the first drift chamber.

8. The method of claim 7, further comprising:
    positioning the separator coaxially with the first drift chamber, the terminal drift chamber, and the reservoir.

9. The method of claim 1, further comprising:
    injecting the jet substantially perpendicular to the surface of the essential oil contained within the reservoir.

10. The method of claim 9, further comprising:
    ejecting a portion of the plume, out of the vapor space of the reservoir and into the first drift chamber in a direction opposite and parallel to the direction of the plume entering the vapor space.

11. An apparatus comprising:
    an eductor;
    a reservoir operably connected to the eductor to receive therefrom a jet generating a plume in the reservoir traveling toward an essential oil contained with a reservoir;
    an exit drift chamber operably connected to receive from a vapor space in the reservoir a flow constituting at least a portion of the plume, the exit drift chamber being sized and shaped to reduce the velocity of the flow exiting the reservoir;
    a separator operably connected to the exit drift chamber;
    a terminal drift chamber operably connected to the separator to receive the flow therefrom and substantially reduce a velocity of the flow from the velocity of entry into the terminal drift chamber from the separator; and
    a siphon operably connecting a supply of essential oil contained by the reservoir into the eductor for entrainment with incoming air therethrough.

12. The apparatus of claim 11, further comprising
a diffusion nozzle passing the plume from the eductor axially parallel to an axis normal to the surface of the essential oil in the reservoir.

13. The apparatus of claim 12, further comprising an exit channel interconnecting the vapor space to the exit drift chamber, the exit channel constricting and accelerating the flow.

14. The apparatus of claim 13, wherein the velocity of the flow through the vapor space of the reservoir and the velocity of the flow through the exit drift chamber are both less than the velocity of the flow through the exit channel.

15. The apparatus of claim 14, further comprising:
a return channel operably connecting the exit drift chamber to the reservoir to return a quantity of separated and coalesced, comparatively larger droplets of the essential oil from the exit drift chamber back into the reservoir.

16. The apparatus of claim 14, wherein at least one of the exit drift chamber and the terminal drift chamber contains walls redirecting the flow therethrough between an inlet thereof and an outlet thereof.

17. The apparatus of claim 11, wherein:
an exit channel passing the flow from the reservoir to the exit drift chamber accelerates the flow to a velocity higher than that of the flow in the reservoir, and higher than that of the flow in the exit drift chamber; and
the separator accelerates the flow between the exit drift chamber and the terminal drift chamber to a velocity higher than that of the flow in the exit drift chamber, and higher than that of the flow in the terminal drift chamber.

18. The apparatus of claim 17, wherein the terminal drift chamber is provided with a discharge port having an area effective to constrict the flow therethrough, imposing thereby a velocity thereof comparable to the velocity of the flow in the separator, and greater than the velocity in the terminal drift chamber, greater than the velocity in the exit drift chamber, and greater than the velocity in the reservoir.

19. An apparatus comprising:
an eductor injecting a flow into a first drift chamber;
the first drift chamber connected in fluid communication with an exit channel accelerating the velocity of the flow received from the eductor, above a first drift velocity thereof through the first drift chamber;
a second drift chamber operably connected in fluid communication with the exit channel to receive and slow the flow from the exit channel;
a separator operably connected in fluid communication with the second drift chamber to receive and accelerate the flow therefrom;
a third drift chamber operably connected in fluid communication with the separator to receive and slow the flow received from the separator; and
the third drift chamber, formed to discharge the flow through a discharge port sized to accelerate the flow above the first drift velocity in the first drift chamber, the second drift velocity in the second drift chamber, and the third drift velocity in the third drift chamber.

20. The apparatus of claim 19, wherein the separator is a micro cyclone passing the flow through a substantially constant cross sectional area while subjecting the flow to a continuous centripetal force toward a central axis thereof.

* * * * *

UNITED STATES PATENT AND TRADEMARK OFFICE
CERTIFICATE OF CORRECTION

| | |
|---|---|
| PATENT NO. | : 9,895,464 B2 |
| APPLICATION NO. | : 14/850789 |
| DATED | : February 20, 2018 |
| INVENTOR(S) | : Sevy |

It is certified that error appears in the above-identified patent and that said Letters Patent is hereby corrected as shown below:

In Claim 1, Line 27 (found at Column 16 Line 1): Before the words "comparatively smaller" please insert the words: --discharging from the vapor space in a direction opposite to that of the jet a flow of the pressurized air entraining a portion of the droplets educted, the entrained portion being--.

Signed and Sealed this
Fifteenth Day of May, 2018

Andrei Iancu
*Director of the United States Patent and Trademark Office*